(12) United States Patent
Fletcher et al.

(10) Patent No.: US 10,154,808 B2
(45) Date of Patent: Dec. 18, 2018

(54) BIOLOGICAL FLUID SEPARATION DEVICE AND BIOLOGICAL FLUID SEPARATION AND TESTING SYSTEM

(71) Applicant: Becton, Dickinson and Company, Franklin Lakes, NJ (US)

(72) Inventors: Gary D. Fletcher, Sparta, NJ (US); Daniel J. Marchiarullo, Morris Plains, NJ (US); Jamieson W. Crawford, Hagerten (SE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 298 days.

(21) Appl. No.: 14/251,714

(22) Filed: Apr. 14, 2014

(65) Prior Publication Data
US 2014/0305197 A1    Oct. 16, 2014

Related U.S. Application Data

(60) Provisional application No. 61/811,918, filed on Apr. 15, 2013.

(51) Int. Cl.
*G01N 33/49* (2006.01)
*A61B 5/15* (2006.01)
(Continued)

(52) U.S. Cl.
CPC ...... *A61B 5/150213* (2013.01); *A61B 5/1411* (2013.01); *A61B 5/151* (2013.01);
(Continued)

(58) Field of Classification Search
USPC ...................................... 73/64.56
See application file for complete search history.

(56) References Cited

U.S. PATENT DOCUMENTS 3,322,114 A    5/1967    Portnoy et al.
3,640,393 A    2/1972    Hurtig
(Continued)

FOREIGN PATENT DOCUMENTS

CN         1382966 A    12/2002
CN       101102847 A     1/2008
(Continued)

OTHER PUBLICATIONS

Membrane Separation Technology for Research and Quality Control, Sartorius AG, Separation Technology, Laboratory Filtration; Mar. 1, 1997.

*Primary Examiner* — Paul West
*Assistant Examiner* — Mark A Shabman
(74) *Attorney, Agent, or Firm* — The Webb Law Firm

(57) ABSTRACT

A blood separation device that is adapted to receive a multi-component blood sample is disclosed. After collecting the blood sample, the blood separation device is able to separate a plasma portion from a cellular portion. After separation, the blood separation device is able to transfer the plasma portion of the blood sample to a point-of-care testing device. The blood separation device also provides a closed sampling and transfer system that reduces the exposure of a blood sample and provides fast mixing of a blood sample with a sample stabilizer. The blood separation device is engageable with a blood testing device for closed transfer of a portion of the plasma portion from the blood separation device to the blood testing device. The blood testing device is adapted to receive the plasma portion to analyze the blood sample and obtain test results.

18 Claims, 7 Drawing Sheets

(51) Int. Cl.
*A61M 1/34* (2006.01)
*G01N 1/28* (2006.01)
*G01N 1/40* (2006.01)
*G01N 1/34* (2006.01)
*B01L 3/00* (2006.01)
*B04B 7/08* (2006.01)
*A61B 5/151* (2006.01)
*A61B 5/157* (2006.01)

(52) U.S. Cl.
CPC ........ *A61B 5/157* (2013.01); *A61B 5/150022* (2013.01); *A61B 5/15101* (2013.01); *A61B 5/15105* (2013.01); *A61B 5/15144* (2013.01); *A61B 5/15198* (2013.01); *A61B 5/150221* (2013.01); *A61B 5/150267* (2013.01); *A61B 5/150305* (2013.01); *A61B 5/150343* (2013.01); *A61B 5/150351* (2013.01); *A61B 5/150412* (2013.01); *A61B 5/150748* (2013.01); *A61B 5/150755* (2013.01); *A61B 5/150778* (2013.01); *A61M 1/34* (2013.01); *B01L 3/502* (2013.01); *B01L 3/5021* (2013.01); *B04B 7/08* (2013.01); *G01N 1/28* (2013.01); *G01N 1/34* (2013.01); *G01N 1/4005* (2013.01); *G01N 1/4077* (2013.01); *G01N 33/491* (2013.01); *A61B 5/150435* (2013.01); *A61B 5/150442* (2013.01); *A61B 5/150969* (2013.01); *B01L 2200/0631* (2013.01); *B01L 2200/10* (2013.01); *B01L 2300/0681* (2013.01); *B01L 2400/0478* (2013.01); *G01N 2001/4016* (2013.01); *G01N 2001/4088* (2013.01)

(56) References Cited

U.S. PATENT DOCUMENTS

| | | | |
|---|---|---|---|
| 4,511,349 A | 4/1985 | Nielsen et al. | |
| 4,627,445 A | 12/1986 | Garcia et al. | |
| 4,842,591 A * | 6/1989 | Luther | A61M 39/0693 285/3 |
| 5,055,203 A | 10/1991 | Columbus | |
| 5,163,442 A | 11/1992 | Ono | |
| 5,219,999 A | 6/1993 | Suzuki et al. | |
| 5,422,018 A | 6/1995 | Saunders et al. | |
| 5,636,640 A | 6/1997 | Staehlin | |
| 5,638,828 A * | 6/1997 | Lauks | B01L 3/502715 600/573 |
| 5,657,963 A * | 8/1997 | Hinchliffe | A61B 17/3462 251/149.1 |
| 5,726,026 A | 3/1998 | Wilding et al. | |
| 5,839,715 A | 11/1998 | Leinsing | |
| 5,922,591 A | 7/1999 | Anderson et al. | |
| 6,074,183 A | 6/2000 | Allen et al. | |
| 6,264,619 B1 | 7/2001 | Ferguson | |
| 6,506,167 B1 | 1/2003 | Ishimito et al. | |
| 6,869,405 B2 | 3/2005 | Marsden | |
| 8,158,410 B2 | 4/2012 | Tang et al. | |
| 2002/0009015 A1 | 1/2002 | Laugharn, Jr. et al. | |
| 2002/0143298 A1 | 10/2002 | Marsden | |
| 2003/0134416 A1 | 7/2003 | Yamanishi et al. | |
| 2004/0142463 A1 | 7/2004 | Walker et al. | |
| 2004/0143226 A1 | 7/2004 | Marsden | |
| 2004/0230216 A1 | 11/2004 | Levaughn et al. | |
| 2005/0069459 A1 | 3/2005 | Ahn et al. | |
| 2005/0133439 A1 * | 6/2005 | Blickhan | A61M 1/3633 210/323.1 |
| 2005/0139547 A1 | 6/2005 | Manoussakis et al. | |
| 2005/0214927 A1 | 9/2005 | Haley | |
| 2006/0029923 A1 | 2/2006 | Togawa et al. | |
| 2006/0240964 A1 | 10/2006 | Lolachi et al. | |
| 2007/0031283 A1 | 2/2007 | Davis et al. | |
| 2007/0160503 A1 | 7/2007 | Sethu et al. | |
| 2008/0135502 A1 | 6/2008 | Pyo et al. | |
| 2008/0240990 A1 | 10/2008 | Flaherty | |
| 2009/0004060 A1 | 1/2009 | Omuro et al. | |
| 2009/0136982 A1 | 5/2009 | Tang et al. | |
| 2009/0181411 A1 | 7/2009 | Battrell et al. | |
| 2009/0204026 A1 | 8/2009 | Crawford et al. | |
| 2009/0281525 A1 * | 11/2009 | Harding | A61M 39/0613 604/537 |
| 2010/0089815 A1 | 4/2010 | Zhang et al. | |
| 2010/0093551 A1 | 4/2010 | Montagu | |
| 2010/0198108 A1 | 8/2010 | Alden | |
| 2010/0241031 A1 | 9/2010 | Lai | |
| 2011/0124130 A1 | 5/2011 | Wagner et al. | |
| 2011/0124984 A1 | 5/2011 | Rostaing | |
| 2011/0134426 A1 * | 6/2011 | Kaduchak | G01N 15/1404 356/337 |
| 2012/0134974 A1 * | 5/2012 | Sehgal | A61K 35/14 424/93.72 |
| 2012/0152858 A1 | 6/2012 | Yang | |
| 2012/0275955 A1 | 11/2012 | Haghgooie et al. | |
| 2012/0277696 A1 | 11/2012 | Gonzalez-Zugasti et al. | |
| 2012/0277697 A1 | 11/2012 | Haghgooie et al. | |
| 2013/0026085 A1 * | 1/2013 | Samsoondar | B01D 63/02 210/136 |
| 2013/0052675 A1 | 2/2013 | Karlsson et al. | |
| 2013/0082012 A1 | 4/2013 | Lean et al. | |
| 2013/0086980 A1 | 4/2013 | Gadini et al. | |
| 2013/0175213 A1 | 7/2013 | Dorrer et al. | |
| 2013/0209331 A1 | 8/2013 | Rodenfels et al. | |

FOREIGN PATENT DOCUMENTS

| | | |
|---|---|---|
| CN | 101332320 A | 12/2008 |
| CN | 102764133 A | 11/2012 |
| DE | 202008010918 U1 | 1/2009 |
| EP | 0376168 A2 | 7/1990 |
| EP | 0747105 A2 | 12/1996 |
| EP | 1096254 A2 | 5/2001 |
| EP | 1106065 A2 | 6/2001 |
| EP | 1477804 A1 | 11/2004 |
| EP | 1602329 A1 | 12/2005 |
| EP | 1627651 A2 | 2/2006 |
| EP | 2264453 A1 | 12/2010 |
| EP | 2413138 A2 | 2/2012 |
| FR | 2929135 A1 | 10/2009 |
| FR | 2977808 A1 | 1/2013 |
| JP | 275332 A | 3/1990 |
| JP | 2004361419 A | 12/2004 |
| WO | 9309710 A1 | 5/1993 |
| WO | 2005018710 A2 | 3/2005 |
| WO | 2006047831 A1 | 5/2006 |
| WO | 2007002579 A2 | 1/2007 |
| WO | 2009123592 A1 | 10/2009 |
| WO | 2011040874 A1 | 4/2011 |
| WO | 2012121686 A1 | 9/2012 |

* cited by examiner

BIOLOGICAL FLUID SEPARATION DEVICE AND BIOLOGICAL FLUID SEPARATION AND TESTING SYSTEM

CROSS REFERENCE TO RELATED APPLICATIONS

The present application claims priority to U.S. Provisional Application No. 61/811,918, filed Apr. 15, 2013, entitled "Medical Device for Collection of a Biological Sample", the entire disclosure of which is hereby incorporated by reference in its entirety.

BACKGROUND OF THE INVENTION

1. Field of the Disclosure

The present disclosure relates generally to devices, assemblies, and systems adapted for use with vascular access devices. More particularly, the present disclosure relates to devices, assemblies, and systems adapted for collecting biological samples for use in point-of-care testing.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, or coagulation, for example.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Despite the rapid advancement in point-of-care testing and diagnostics, blood sampling techniques have remained relatively unchanged. Blood samples are frequently drawn using hypodermic needles or vacuum tubes attached to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Each additional device increases the time and cost of the testing process.

Point-of-care testing devices allow for a blood sample to be tested without needing to send the blood sample to a lab for analysis. Thus, it is desirable to create a device that provides an easy, safe, reproducible, and accurate process with a point-of-care testing system.

SUMMARY OF THE INVENTION

The present disclosure provides a biological fluid separation device, such as a blood separation device, that is adapted to receive a blood sample having a cellular portion and a plasma portion. After collecting the blood sample, the blood separation device is able to separate the plasma portion from the cellular portion. After separation, the blood separation device is able to transfer the plasma portion of the blood sample to a point-of-care testing device. The blood separation device of the present disclosure also provides a closed sampling and transfer system that reduces the exposure of a blood sample and provides fast mixing of a blood sample with a sample stabilizer. The sample stabilizer can be an anticoagulant, or a substance designed to preserve a specific element within the blood such as, for example, RNA, protein analyte, or other element. The blood separation device is engageable with a blood testing device for closed transfer of a portion of the plasma portion from the blood separation device to the blood testing device. The blood testing device is adapted to receive the plasma portion to analyze the blood sample and obtain test results.

The blood separation device of the present disclosure advantageously allows for the following: a) a safe, closed system for rapidly separating whole blood into a clean plasma sample for transfer to a point-of-care testing device; b) plasma to be efficiently generated by repeatedly recirculating whole blood through a filter; c) separated plasma to be safely transferred to the point-of-care testing device via a septum enabled outlet port; d) manual operation of a pump and check valves to ensure ease of use in moving whole blood in one direction repeatedly through the filter, thereby improving the efficiency of plasma generation from the cellular sample; e) a system that can easily accept whole blood from a number of different blood collection modalities through an onboard blood inlet port; and f) optionally, an acoustic focusing element to be used to focus red blood cells in the fluidic pathway toward the center of the flow and away from the filter, further enhancing the efficiency of the plasma separation in the filter.

Some of the other advantages of the blood separation device and the biological fluid separation and testing system of the present disclosure over prior systems are that it is a closed system which reduces blood sample exposure, it provides passive and fast mixing of the blood sample with a sample stabilizer, it facilitates separation of the blood sample without transferring the blood sample to a separate device, and it is capable of transferring pure plasma to a point-of-care testing device. The blood separation device of the present disclosure enables integrated blood collection and plasma creation in a closed system without centrifugation. The clinician may collect and separate the blood sample and then immediately transfer the plasma portion to the point-of-care testing device without further manipulation. This enables collection and transfer of plasma to the point-of-care testing device without exposure to blood. In addition, the blood separation device of the present disclosure minimizes process time by processing the blood within the blood separation device and without external machinery. Further, for tests which only require small amounts of blood, it eliminates the waste associated with blood collection and plasma separation with an evacuated tube.

In accordance with an embodiment of the present invention, a biological fluid separation device adapted to receive a multi-component blood sample includes a housing having an inlet port, a flow channel, and an outlet port, the inlet port and the outlet port in fluid communication via the flow channel. The device also includes a filter disposed within the flow channel between the inlet port and the outlet port, a first reservoir defined within the flow channel between the inlet port and the filter, and a second reservoir defined within the flow channel between the filter and the outlet port. The filter is adapted to trap a first portion of the multi-component blood sample within the first reservoir and to allow a second portion of the multi-component blood sample to pass through the filter and into the second reservoir.

In certain configurations, the first portion of the multi-component blood sample is a cellular portion, and the second portion of the multi-component blood sample is a plasma portion. In other configurations, the inlet port is adapted to receive the blood sample via connection to a blood collection device. In still other configurations the filter includes a tangential flow filter. The tangential flow filter may utilizes a cross-flow filtration to separate the first portion from the second portion. The device may also include an acoustic focus element disposed within the housing.

Optionally, the outlet port is adapted for connection to a point-of-care testing device for closed transfer of at least a portion of the second portion from the second reservoir to the point-of-care testing device via the outlet port. The device may also include a one-way valve disposed within the flow channel. In other configurations, the device also includes a pump in fluid communication with the flow channel for advancing the multi-component blood sample received within the flow channel through the one-way valve. In still other configurations, the outlet port includes a septum transitionable between a closed position and an open position.

In accordance with another embodiment of the present invention, a biological fluid separation system for separating a multi-component blood sample includes a blood separation device adapted to receive the blood sample. The blood separation device includes a housing having an inlet port, a flow channel, and an outlet port, with the inlet port and the outlet port in fluid communication via the flow channel. The blood separation device also includes a filter disposed within the flow channel between the inlet port and the outlet port, a first reservoir defined within the flow channel between the inlet port and the filter, and a second reservoir defined within the flow channel between the filter and the outlet port. The filter is adapted to trap a first portion of the multi-component blood sample within the first reservoir and allow a second portion of the multi-component blood sample to pass through the filter and into the second reservoir. The system also includes a blood testing device having a receiving port engageable with the outlet port of the blood separation device for closed transfer of at least a portion of the second portion from the second reservoir to the blood testing device via the outlet port.

In certain configurations, the first portion of the multi-component blood sample is a cellular portion, and the second portion of the multi-component blood sample is a plasma portion. Optionally, the blood testing device includes a point-of-care testing device. In certain configurations, the filter includes a tangential flow filter. The tangential flow filter may utilize a cross-flow filtration to separate the plasma portion from the cellular portion.

In still further configurations, the system includes an acoustic focus element disposed within the housing. The inlet port may be adapted to receive the blood sample via connection to a blood collection device. The separation system may also include a one-way valve disposed within the flow channel. In still further configurations, the system includes a pump in fluid communication with the flow channel for advancing the blood sample received within the flow channel through the one-way valve. The outlet port may include a septum transitionable between a closed position and an open position.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
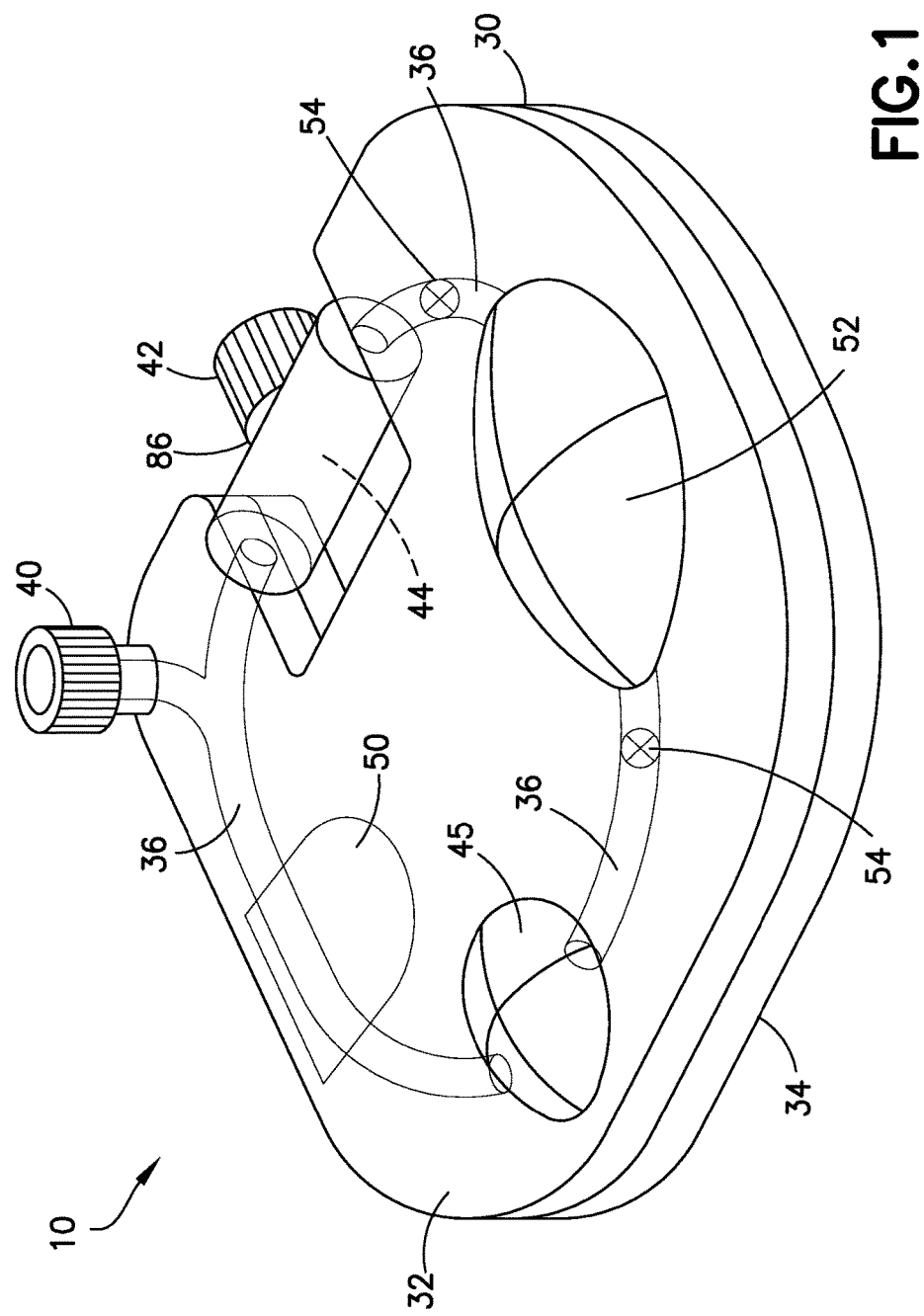
FIG. 1 is a perspective view of a biological fluid separation device in accordance with an embodiment of the present invention.
Figure 2:
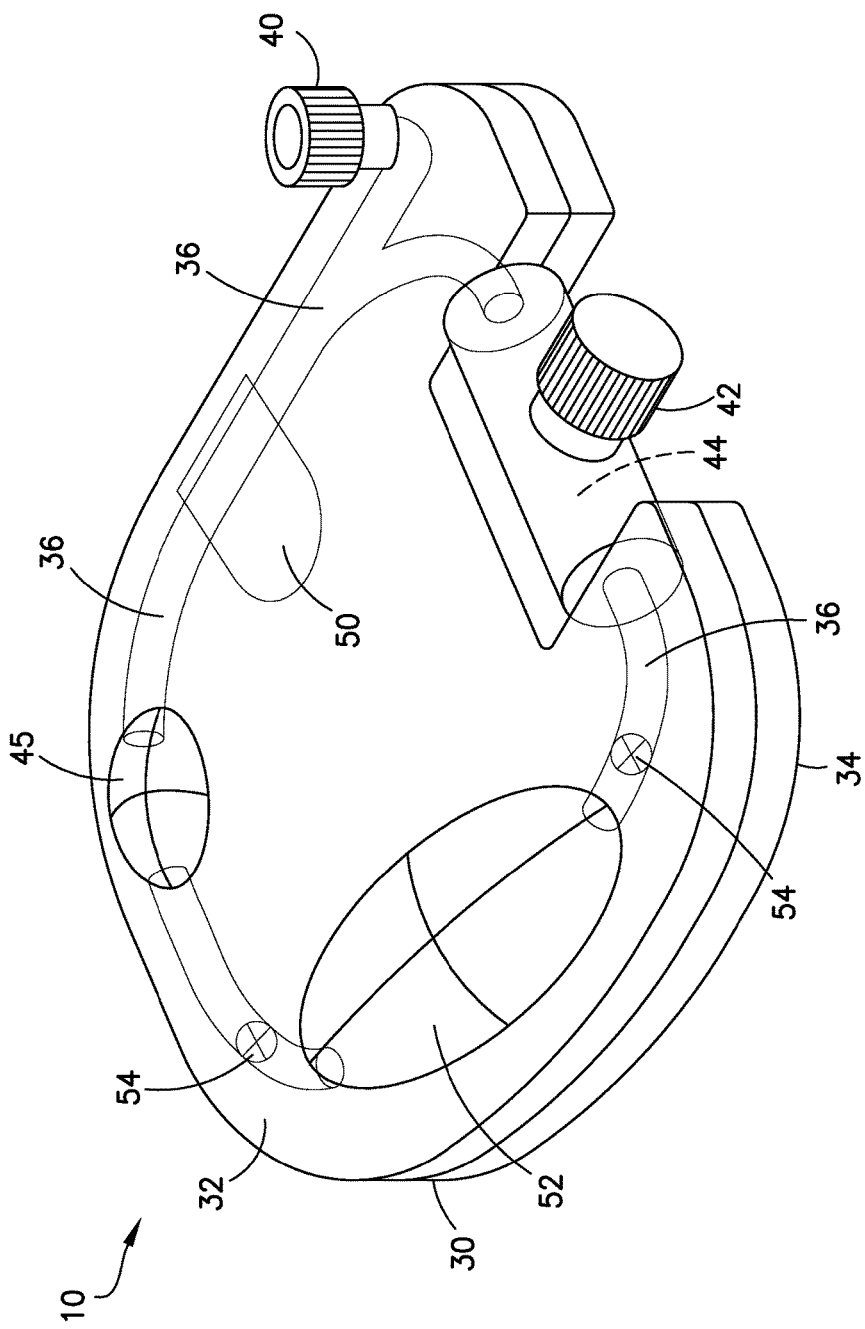
FIG. 2 is a second perspective view of a biological fluid separation device in accordance with an embodiment of the present invention.
Figure 3:
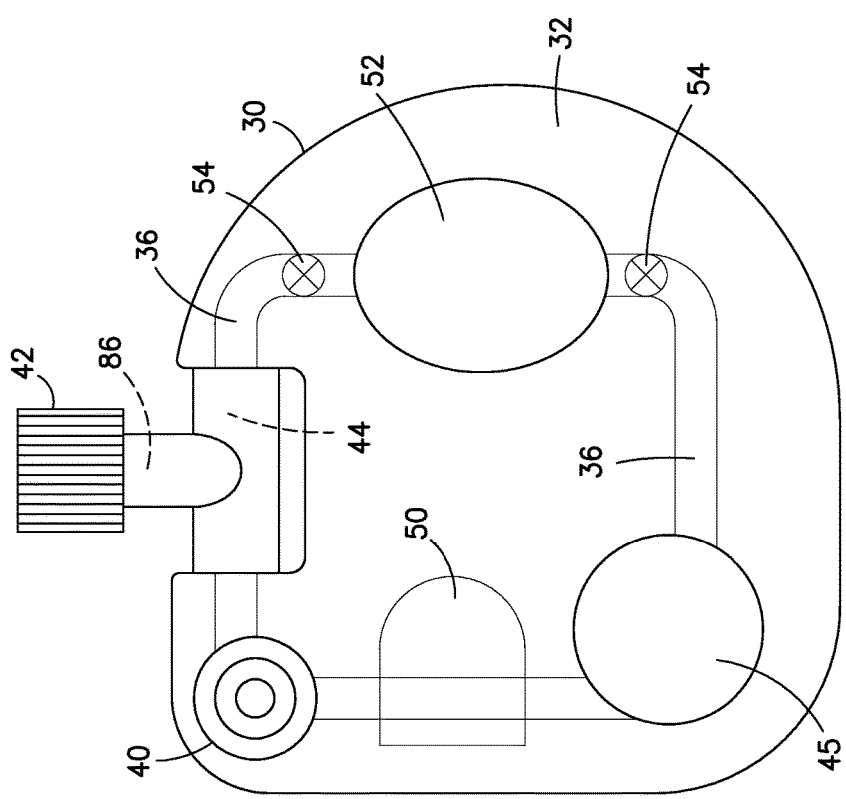
FIG. 3 is a top view of a biological fluid separation device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Various point-of-care testing devices are known in the art. Such point-of-care testing devices include test strips, glass slides, diagnostic cartridges, or other testing devices for testing and analysis. Test strips, glass slides, and diagnostic cartridges are point-of-care testing devices that receive a blood sample and test that blood for one or more physiological and biochemical states. There are many point-of-care devices that use cartridge based architecture to analyze very small amounts of blood bedside without the need to send the sample to a lab for analysis. This saves time in getting results over the long run but creates a different set of challenges versus the highly routine lab environment. Examples of such testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

However, the samples provided to such point-of-care testing cartridges are currently manually collected with an open system and transferred to the point-of-care testing cartridge in a manual manner that often leads to inconsistent results, or failure of the cartridge leading to a repeat of the sample collection and testing process, thereby negating the advantage of the point-of-care testing device. Accordingly, a need exists for a system for collecting and transferring a sample to a point-of-care testing device that provides safer, reproducible, and more accurate results. Accordingly, a point-of-care collecting and transferring system of the present disclosure will be described hereinafter. A system of the present disclosure enhances the reliability of the point-of-care testing device by: 1) incorporating a more closed type of sampling and transfer system; 2) minimizing open exposure of the sample; 3) improving sample quality; 4) improving the overall ease of use; and 5) separating the sample at the point of collection.

FIGS. 1-4 and 6 illustrate an exemplary embodiment of the present disclosure. Referring to FIGS. 1-4, a biological fluid separation and transfer device or blood separation device 10 of the present disclosure is adapted to receive a blood sample 12 having a cellular portion 14 and a plasma portion 16. After collecting the blood sample 12, the blood separation device 10 is able to separate the plasma portion 16 from the cellular portion 14. After separation, the blood separation device 10 is able to transfer the plasma portion 16 of the blood sample 12 to a point-of-care testing device. The blood separation device 10 of the present disclosure also provides a closed sampling and transfer system that reduces the exposure of a blood sample and provides fast mixing of a blood sample with a sample stabilizer.

Figure 5:
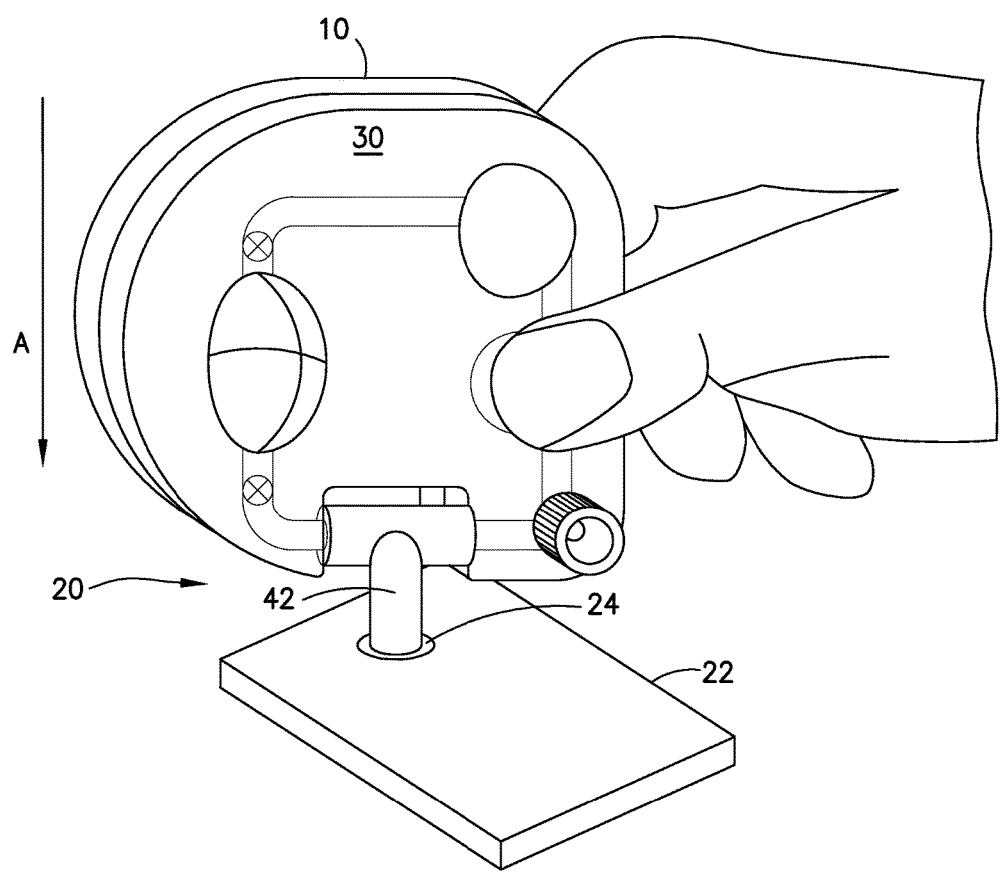
FIG. 5 is a perspective view of a biological fluid separation device and a point-of-care testing device in accordance with an embodiment of the present invention.

FIG. 5 illustrates an exemplary embodiment of the present disclosure. Referring to FIG. 5, a biological fluid separation and testing system 20, such as a blood separation and testing system, of the present disclosure includes a blood separation device 10 and a blood testing device or point-of-care testing device 22 engageable with the blood separation device 10 for closed transfer of a portion of the plasma portion 16 (FIG. 6) from the blood separation device 10 to the blood testing device 22. The blood testing device 22 is adapted to receive the plasma portion 16 to analyze the blood sample and obtain test results.

Some of the advantages of the blood separation device and the blood separation and testing system of the present disclosure over prior systems are that it is a closed system which reduces blood sample exposure, it provides passive and fast mixing of the blood sample with a sample stabilizer, it facilitates separation of the blood sample without transferring the blood sample to a separate device, and it is capable of transferring pure plasma to a point-of-care testing device. The blood separation device of the present disclosure enables integrated blood collection and plasma creation in a closed system without centrifugation. The clinician may collect and separate the blood sample and then immediately transfer the plasma portion to the point-of-care testing device without further manipulation. This enables collection and transfer of plasma to the point-of-care testing device without exposure to blood. In addition, the blood separation device of the present disclosure minimizes process time by processing the blood within the blood separation device and without external machinery. Further, for tests which only require small amounts of blood, it eliminates the waste associated with blood collection and plasma separation with an evacuated tube.

Referring to FIGS. 1-4 and 6, a blood separation device 10 generally includes a housing or cartridge 30 having an upper portion 32 and a lower portion 34. The upper portion 32 and the lower portion 34 are secured theretogether such that significant relative movement between the upper portion 32 and the lower portion 34 is prevented. In one embodiment, the upper portion 32 and the lower portion 34 are ultrasonically welded together. In other embodiments, similar connection mechanisms may be used. The upper portion 32 and the lower portion 34 define a flow channel 36 therebetween. The housing 30 of the blood separation device 10 is adapted to receive a blood sample 12 therein. The blood sample 12 may include a cellular portion 14 and a plasma portion 16.

The housing 30 of the blood separation device 10 includes an inlet port 40, an outlet port 42 in fluid communication with the inlet port 40 via the flow channel 36, a filter 44 disposed within the flow channel 36 between the inlet port 40 and the outlet port 42, a bulb blood reservoir 45 disposed within the housing 30 between the inlet port 40 and the filter 44 and in fluid communication with the flow channel 36, a first reservoir 46 disposed within the housing 30 between the inlet port 40 and the filter 44 and in fluid communication with the flow channel 36, and a second reservoir or exit reservoir 48 disposed within the housing 30 between the filter 44 and the outlet port 42 and in fluid communication with the flow channel 36.

Figure 4:
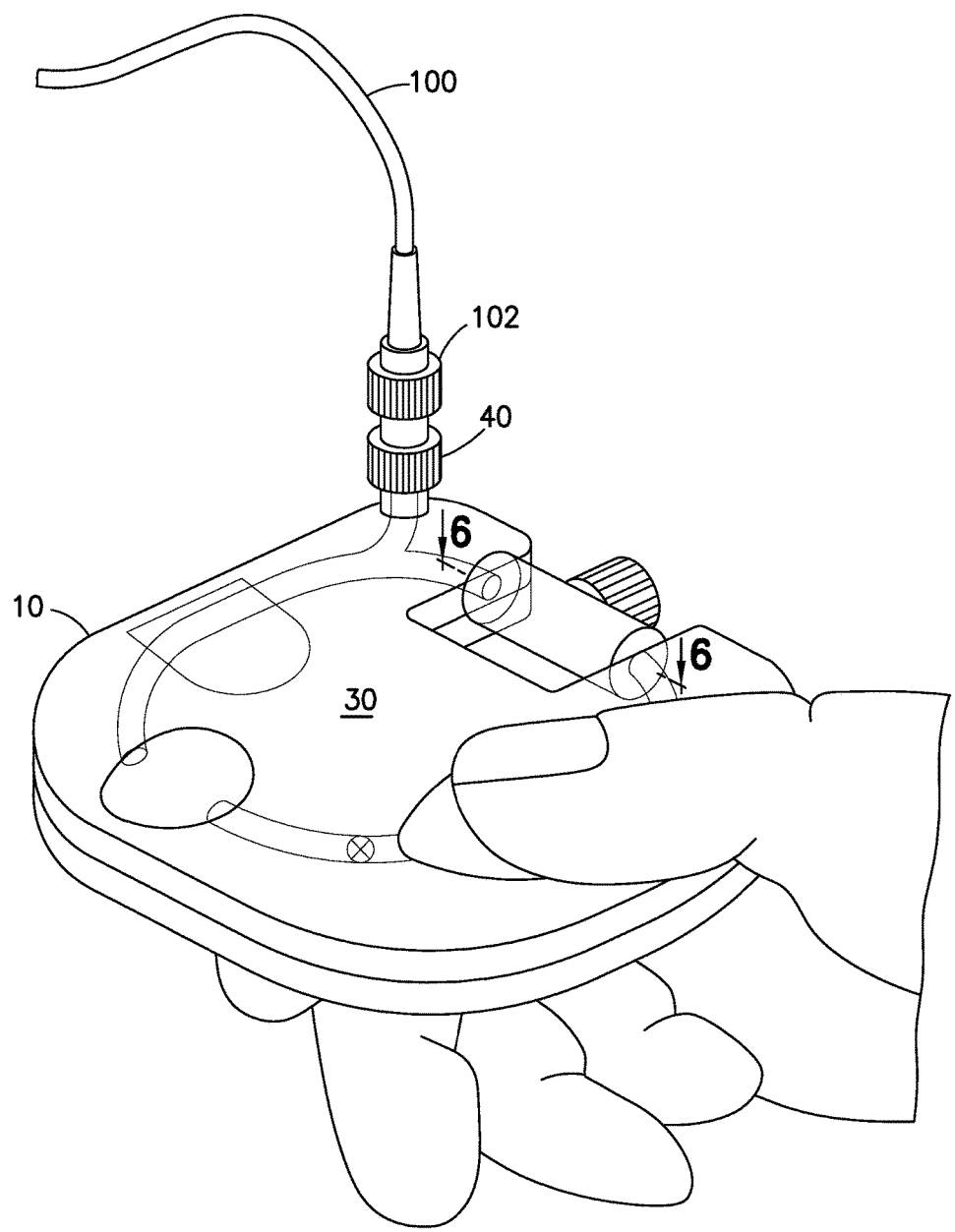
FIG. 4 is a perspective view of a biological fluid separation device in accordance with an embodiment of the present invention, with a biological fluid collection device attached to the biological fluid separation device.

Referring to FIG. 4, the inlet port 40 is adapted to be connected to a blood collection set or blood collection device 100 to allow for the collection of a blood sample 12 into the blood separation device 10. The inlet port 40 may be sized and adapted for engagement with a separate device, such as a needle assembly or IV connection assembly and, therefore, may include a mechanism for such engagement as is conventionally known. For example, in one embodiment, the inlet port 40 may include a luer lock or luer tip for engagement with an optional separate luer mating component of such a separate device for attachment therewith. For example, referring to FIG. 4, the blood collection set 100 may include a luer component 102 for engagement with the inlet port 40 of the blood separation device 10. In this manner, the inlet port 40 is connectable to the blood collection set 100 for the collection of a blood sample into the blood separation device 10. In addition, a mechanism for locking engagement between the inlet port 40 and the blood collection set 100 may also be provided. Such luer connections and luer locking mechanisms are well known in the art. The blood collection set 100 may include a needle assembly, an IV connection assembly, a PICC line, an arterial indwelling line, or similar blood collection means.

Referring to FIGS. 1-4, the inlet port 40 is in fluid communication with the first reservoir 46 via the flow channel 36. The inlet port 40 may also include a resealable septum that is transitionable between a closed position and an open position. With the septum in an open position, a blood sample 12 may flow through the inlet port 40 to the first reservoir 46.

Figure 6:
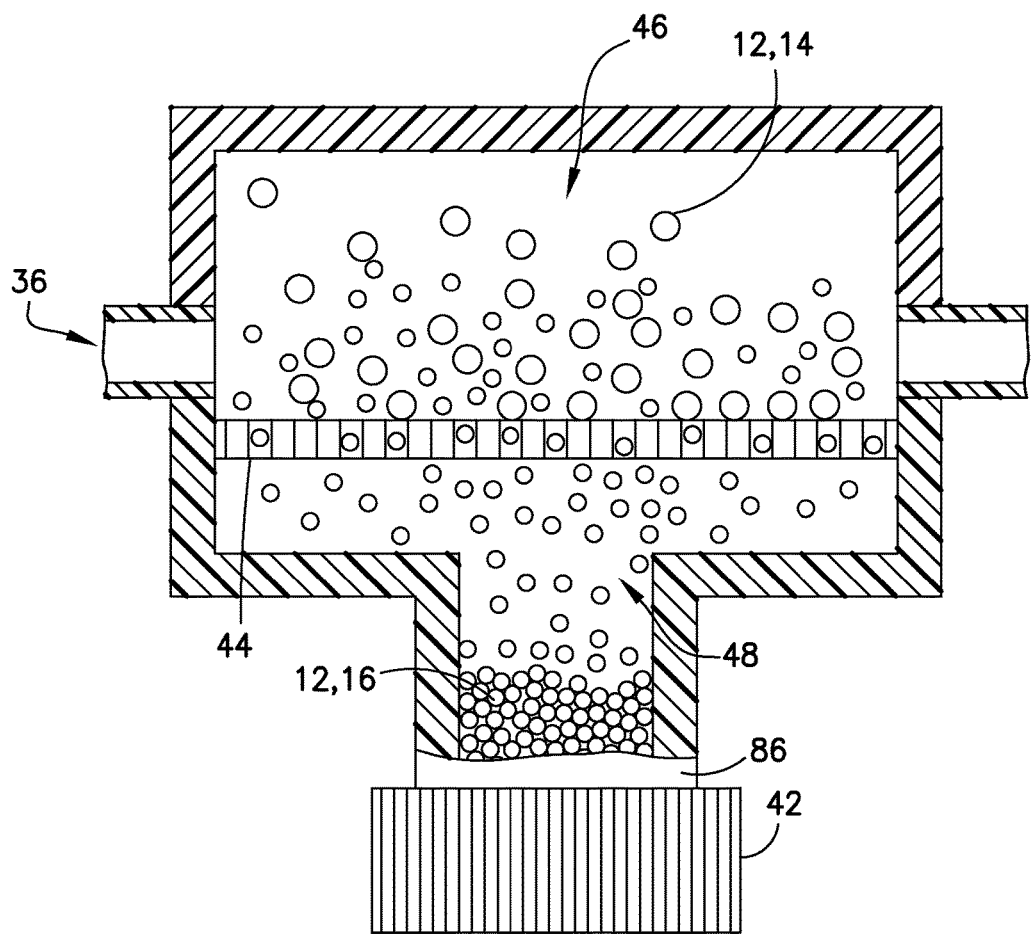
FIG. 6 is a cross-sectional view of a filter of a biological fluid separation device in accordance with an embodiment of the present invention, with the filter separating a plasma portion of a blood sample from a cellular portion of the blood sample.

Referring to FIG. 6, the first reservoir 46 is sealed such that a cellular portion 14 of the blood sample 12 is contained within the first reservoir 46 and the plasma portion 16 of the blood sample 12 can exit the first reservoir 46 by passing through the filter 44 to the second or exit reservoir 48 as discussed below. Only the plasma portion 16 of the blood sample 12 is able to pass through the filter 44.

The housing 30 of the blood separation device 10 also may include an acoustic focus element 50, a pump 52, a check valve or one-way valve 54, and a valve or septum 86 (FIGS. 7 and 8) at the outlet port 42. The outlet port 42 is adapted for connection to a point-of-care testing device 22 for closed transfer of a portion of the plasma portion 16 from the blood separation device 10 to the point-of-care testing device 22 via the outlet port 42 as described in more detail below. Referring to FIG. 6, the outlet port 42 is in fluid communication with the second or exit reservoir 48. The valve or septum 86 at the outlet port 42 is transitionable between a closed position and an open position. With the valve or septum 86 in an open position (FIG. 8), the plasma portion 16 of the blood sample 12 may flow through the outlet port 42 to a blood testing device or a point-of-care testing device 22 (FIG. 5).

In one embodiment, the acoustic focus element 50 is disposed within the housing 30 and focuses the blood cells away from the membrane because of static pressure minima and maxima created by the acoustic wave resulting in improved separation efficiency. The acoustic focus element 50 may focus red blood cells to the center of the flow channel 36 and the filter 44 prior to passing through the filter 44. In one embodiment, the housing 30 may include a pump 52 and a one-way or check valve 54 to manually move blood in one direction within the flow channel 36. In one embodiment, there may be more than one check valve 54 disposed within the flow channel 36. In one embodiment, the pump 52 is in fluid communication with the flow channel 36 for advancing the blood sample 12 received within the flow channel 36 through the valves 54.

In one embodiment, a portion of the flow channel 36 or the inlet port 40 may also include a layer of sample stabilizer. The sample stabilizer, can be an anticoagulant, or a substance designed to preserve a specific element within the blood such as, for example, RNA, protein analyte, or other element. In one embodiment, the layer of sample stabilizer may be disposed over the filter 44. In other embodiments, the layer of sample stabilizer may be located anywhere between the inlet port 40 and the filter 44. In this manner, as a blood sample 12 flows through the inlet port 40 and into the first reservoir 46, the blood separation device 10 provides passive and fast mixing of the blood sample 12 with the sample stabilizer.

The housing 30 of the blood separation device 10 includes a filter 44 disposed between the first reservoir 46 and the second reservoir 48 as shown in FIG. 6. The filter 44 is adapted to trap the cellular portion 14 of the blood sample 12 within the first reservoir 46 and allow the plasma portion 16 of the blood sample 12 to pass through the filter 44 to the second reservoir 48 as shown in FIG. 6. In one embodiment, the filter 44 includes a tangential flow filter. The tangential flow filter utilizes a cross-flow filtration to separate the plasma portion 16 from the cellular portion 14.

In one embodiment, the filter 44 may be either hollow fiber membrane filters or flat membrane filters, such as track-edge filters. Membrane filter pore size and porosity can be chosen to optimize separation of clean (i.e., red blood cell free, white blood cell free, and/or platelet free) plasma in an efficient manner. In another embodiment, the filter 44 includes a lateral flow membrane. In other embodiments, the filter 44 may comprise any filter that is able to trap the cellular portion 14 of the blood sample 12 within the first reservoir 46 and allow the plasma portion 16 of the blood sample 12 to pass through the filter 44 to the second reservoir 48.

Referring to FIG. 5, a blood testing device or point-of-care testing device 22 includes a receiving port 24 adapted to receive the outlet port 42 of the blood separation device 10. The blood testing device 22 is adapted to receive the outlet port 42 of the blood separation device 10 for closed transfer of a portion of the plasma portion 16 (FIG. 6) from the blood separation device 10 to the blood testing device 22. The blood testing device 22 is adapted to receive the plasma portion 16 to analyze the blood sample and obtain test results.

As discussed above, the outlet port 42 of the blood separation device 10 may include a valve or septum 86 that is transitionable between a closed position and an open position. With the valve or septum 86 in an open position (FIG. 8), the plasma portion 16 of the blood sample 12 may flow through the outlet port 42 to a blood testing device or a point-of-care testing device 22 (FIG. 5).

Figure 7:
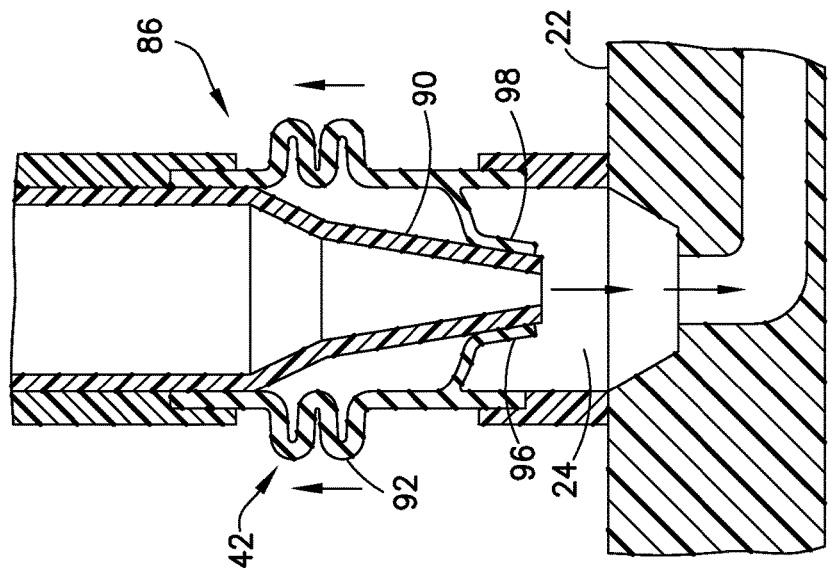
FIG. 7 is a cross-sectional view of a septum of a biological fluid separation device in accordance with an embodiment of the present invention, with the septum in a closed position.
Figure 8:
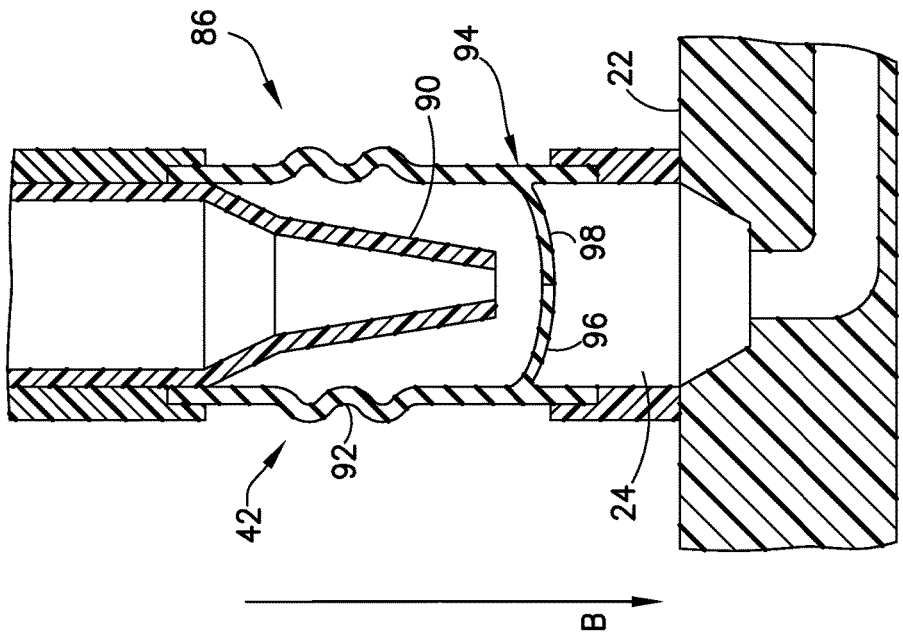
FIG. 8 is a cross-sectional view of a septum of a biological fluid separation device in accordance with an embodiment of the present invention, with the septum in an open position.

In one embodiment, referring to FIGS. 7 and 8, the valve 86 may generally include a transfer channel 90, a bellows or deformable wall member 92, and a septum or barrier 94 having a first barrier wall 96 and a second barrier wall 98. Referring to FIG. 7, the valve 86 is in a closed position to prevent the plasma portion 16 of the blood sample 12 from flowing through the outlet port 42. In this manner, the plasma portion 16 is sealed within the blood separation device 10. Referring to FIG. 8, the valve 86 is in an open position so that the plasma portion 16 of the blood sample 12 may flow through the outlet port 42 to a blood testing device or a point-of-care testing device 22 (FIG. 5).

Referring to FIG. 7, with the plasma portion 16 received within the exit reservoir 48 of the blood separation device 10 (FIG. 6), the outlet port 42 of the blood separation device 10 is then positioned over the receiving port 24 of the point-of-care testing device 22. Pushing down in the direction of arrow B compresses the deformable wall member 92 and opens up the first barrier wall 96 and the second barrier wall 98 of the septum 94 as shown in FIG. 8. With the valve 86 in the open position, the plasma portion 16 of the blood sample 12 is allowed to flow through the receiving port 24 to the point-of-care testing device 22 in a closed manner reducing exposure to the clinician and the patient.

The valve 86 of the blood separation device 10 only opens when the outlet port 42 is pressed upon the receiving port 24 of the point-of-care testing device 22. This releases the isolated plasma portion 16 directly into the receiving port 24 of the point-of-care testing device 22, thus mitigating unnecessary exposure to the patient's blood.

Referring to FIGS. 1-6, use of a blood separation device and blood separation and testing system of the present disclosure will now be described. Referring to FIG. 4, the inlet port 40 of the blood separation device 10 is adapted to be connected to a blood collection set 100 to allow for the collection of a blood sample 12 into the blood separation device 10 as discussed above. Once the blood collection set 100 is connected to a patient and a resealable septum of the inlet port 40 is in the open position, blood begins to flow from the blood collection set 100 through the inlet port 40 to the first reservoir 46 via the flow channel 36 due to the pump 52 that allows flow of the blood sample 12 in one direction. As the blood sample 12 slowly fills the blood separation device 10, it is collected and stabilized over a layer of sample stabilizer. Referring to FIG. 6, the plasma portion 16 of the blood sample 12 may then flow through the filter 44 so that the plasma portion 16 is separated from the cellular portion 14. The plasma portion 16 passes through the filter 44 and into the second or exit reservoir 48.

After disconnecting the blood separation device 10 from the blood collection set 100 or other blood collection line, the blood separation device 10 may be engaged with a blood testing device 22. Referring to FIG. 5, the clinician may then press the outlet port 42 against the receiving port 24 of the point-of-care testing device 22 in the direction of arrow A to open the valve 86 (FIG. 8) and to transfer the collected plasma portion 16 to the point-of-care testing device 22. The blood testing device 22 is adapted to receive the outlet port 42 of the blood separation device 10 for closed transfer of a portion of the plasma portion 16 from the blood separation device 10 to the blood testing device 22. The blood testing device 22 is adapted to receive the plasma portion 16 to analyze the blood sample and obtain test results.

The blood separation device 10 advantageously allows for the following: a) a safe, closed system for rapidly separating a whole blood sample, including a cellular portion, into a clean plasma sample for transfer to a point-of-care testing device 22; b) plasma to be efficiently generated by repeatedly recirculating a cellular portion through the filter 44; c) separated plasma to be safely transferred to the point-of-care testing device 22 via a septum enabled outlet port 42; d) manual operation of the pump 52 and check valves 54 to ensure ease of use in moving a whole blood sample, including a cellular portion in one direction repeatedly through the filter 44, thereby improving the efficiency of plasma generation from the whole blood sample; e) a system that can easily accept a cellular portion from a number of different blood collection modalities through an onboard blood inlet port 40; and f) optionally, acoustic focusing element 50 to be used to focus red blood cells in the fluidic pathway toward the center of the flow and away from the filter 44, further enhancing the efficiency of the plasma separation in the filter 44.

Some of the other advantages of the blood separation device and the blood separation and testing system of the present disclosure over prior systems are that it is a closed system which reduces blood sample exposure, it provides passive and fast mixing of the blood sample with a sample stabilizer, it facilitates separation of the blood sample without transferring the blood sample to a separate device, and it is capable of transferring pure plasma to the point-of-care testing device 22. The blood separation device of the present disclosure enables integrated blood collection and plasma creation in a closed system without centrifugation. The clinician may collect and separate the blood sample and then immediately transfer the plasma portion to the point-of-care testing device 22 without further manipulation. This enables collection and transfer of plasma to the point-of-care testing device 22 without exposure to blood. In addition, the blood separation device of the present disclosure minimizes process time by processing the blood within the blood separation device and without external machinery. Further, for tests which only require small amounts of blood, it eliminates the waste associated with blood collection and plasma separation with an evacuated tube.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid separation device adapted to receive a multi-component blood sample, the biological fluid separation device comprising:
   a housing having an inlet port, a flow channel, and an outlet port having a valve, the inlet port and the outlet port in fluid communication via the flow channel, wherein the valve comprises a deformable wall member defining an interior space and transitionable between an extended position and a compressed position and a barrier disposed within the interior space of the deformable wall member, the barrier is reversibly transitionable between a closed position and an open position, and the barrier is transitioned from the closed position to the open position as the deformable wall member is transitioned from the extended position to the compressed position;
   a separation member disposed within the flow channel between the inlet port and the outlet port;
   a first reservoir defined within the flow channel between the inlet port and the separation member; and
   a second reservoir defined within the flow channel between the separation member and the outlet port, wherein the separation member is adapted to trap a first portion of the multi-component blood sample within the first reservoir and to allow a second portion of the multi-component blood sample to pass through the separation member and into the second reservoir.

2. The biological fluid separation device of claim 1, wherein the first portion of the multi-component blood sample is a cellular portion, and the second portion of the multi-component blood sample is a plasma portion.

3. The biological fluid separation device of claim 1, wherein the inlet port is adapted to receive the blood sample via connection to a blood collection device.

4. The biological fluid separation device of claim 1, wherein the separation member comprises a tangential flow filter.

5. The biological fluid separation device of claim 4, wherein the tangential flow filter utilizes a cross-flow filtration to separate the first portion from the second portion.

6. The biological fluid separation device of claim 4, further comprising an acoustic focus element disposed within the housing.

7. The biological fluid separation device of claim 1, wherein the outlet port is adapted for connection to a point-of-care testing device for closed transfer of at least a portion of the second portion from the second reservoir to the point-of-care testing device via the outlet port.

8. The biological fluid separation device of claim 1, further comprising a one-way valve disposed within the flow channel.

9. The biological fluid separation device of claim 8, further comprising a pump in fluid communication with the flow channel for advancing the multi-component blood sample received within the flow channel through the one-way valve.

10. A biological fluid separation system for separating a multi-component blood sample, the biological fluid separation and testing system comprising:
a biological fluid separation device adapted to receive the blood sample, the biological fluid separation device comprising:
a housing having an inlet port, a flow channel, and an outlet port having a valve, the inlet port and the outlet port in fluid communication via the flow channel, wherein the valve comprises a deformable wall member defining an interior space and transitionable between an extended position and a compressed position and a barrier disposed within the interior space of the deformable wall member, the barrier is reversibly transitionable between a closed position and an open position, and the barrier is transitioned from the closed position to the open position as the deformable wall member is transitioned from the extended position to the compressed position;
a separation member disposed within the flow channel between the inlet port and the outlet port;
a first reservoir defined within the flow channel between the inlet port and the separation member; and
a second reservoir defined within the flow channel between the separation member and the outlet port, wherein the separation member is adapted to trap a first portion of the multi-component blood sample within the first reservoir and allow a second portion of the multi-component blood sample to pass through the separation member and into the second reservoir; and
a blood testing device having a receiving port engageable with the outlet port of the blood separation device for closed transfer of at least a portion of the second portion from the second reservoir to the blood testing device via the outlet port.

11. The biological fluid separation system of claim 10, wherein the first portion of the multi-component blood sample is a cellular portion, and the second portion of the multi-component blood sample is a plasma portion.

12. The biological fluid separation system of claim 10, wherein the blood testing device comprises a point-of-care testing device.

13. The biological fluid separation system of claim 10, wherein the separation member comprises a tangential flow filter.

14. The biological fluid separation system of claim 13, wherein the tangential flow filter utilizes a cross-flow filtration to separate the second portion from the first portion.

15. The biological fluid separation system of claim 10, further comprising an acoustic focus element disposed within the housing.

16. The biological fluid separation system of claim 10, wherein the inlet port is adapted to receive the blood sample via connection to a biological fluid collection device.

17. The biological fluid separation system of claim 10, further comprising a one-way valve disposed within the flow channel.

18. The biological fluid separation system of claim 17, further comprising a pump in fluid communication with the flow channel for advancing the blood sample received within the flow channel through the one-way valve.

* * * * *